(12) United States Patent
Jung et al.

(10) Patent No.: US 7,208,260 B2
(45) Date of Patent: *Apr. 24, 2007

(54) CROSS-LINKING MONOMERS FOR PHOTORESIST, AND PROCESS FOR PREPARING PHOTORESIST POLYMERS USING THE SAME

(75) Inventors: Jae Chang Jung, Ichon-shi (KR); Keun Kyu Kong, Ichon-shi (KR); Min Ho Jung, Ichon-shi (KR); Geun Su Lee, Ichon-shi (KR); Ki Ho Balk, Ichon-shi (KR)

(73) Assignee: Hynix Semiconductor Inc. (KR)

( * ) Notice: Subject to any disclaimer, the term of this patent is extended or adjusted under 35 U.S.C. 154(b) by 126 days.

This patent is subject to a terminal disclaimer.

(21) Appl. No.: 10/080,507

(22) Filed: Feb. 22, 2002

(65) Prior Publication Data

US 2002/0177069 A1 Nov. 28, 2002

Related U.S. Application Data

(63) Continuation-in-part of application No. 09/465,111, filed on Dec. 16, 1999, now abandoned.

(30) Foreign Application Priority Data

Dec. 31, 1998 (KR) .................................. 98-63793

(51) Int. Cl.
- G03C 1/73 (2006.01)
- G03F 7/038 (2006.01)
- G03F 7/039 (2006.01)
- G03F 7/30 (2006.01)
- C08F 232/00 (2006.01)

(52) U.S. Cl. .................. 430/270.1; 430/905; 430/910; 430/914; 430/921; 430/925; 430/325; 430/326; 430/330; 430/331; 430/311; 430/319; 526/281

(58) Field of Classification Search .............. 560/224; 526/272, 281, 323.2; 430/270.1, 910, 914, 430/325, 326, 319
See application file for complete search history.

(56) References Cited

U.S. PATENT DOCUMENTS

| | | | |
|---|---|---|---|
| 4,329,419 A | 5/1982 | Goff et al. | |
| 4,777,115 A | 10/1988 | Koch et al. | |
| 5,777,068 A | 7/1998 | Tanaka et al. | |
| 6,120,972 A * | 9/2000 | Iwanaga et al. | 430/270.1 |
| 6,180,316 B1 * | 1/2001 | Kajita et al. | 430/270.1 |
| 6,306,564 B1 * | 10/2001 | Mullee | 430/329 |
| 6,331,383 B1 * | 12/2001 | Sakai | 430/325 |
| 6,403,281 B1 * | 6/2002 | Lee et al. | 430/270.1 |
| 6,569,599 B2 * | 5/2003 | Lee et al. | 430/270.1 |
| 6,589,707 B2 * | 7/2003 | Lee et al. | 430/270.1 |

FOREIGN PATENT DOCUMENTS

| | | |
|---|---|---|
| DE | 3540950 A1 | 5/1987 |
| EP | 0 223 114 A2 | 5/1987 |
| EP | 0 278 691 A2 | 8/1988 |
| EP | 0 422 628 A2 | 4/1991 |
| EP | 0 422628 A3 | 4/1991 |
| EP | 0 475 628 A1 | 3/1992 |
| EP | 0 930541 A1 | 7/1999 |
| EP | 0 901043 B1 | 10/1999 |
| FR | 2057752 | 5/1971 |
| GB | 2 345 286 A * | 7/2000 |
| JP | 59-125728 | 7/1984 |
| JP | 63-17903 | 1/1988 |
| WO | WO 92/0702 | 4/1992 |

OTHER PUBLICATIONS

*Aldrich Catalog Handbook of Fine Chemicals*, 1996-1997, p. 255 (published by Aldrich Chemical Company).

* cited by examiner

*Primary Examiner*—Sin Lee
(74) *Attorney, Agent, or Firm*—Townsend and Townsend and Crew LLP

(57) ABSTRACT

The present invention discloses a cross-linking monomer represented by the following Chemical Formula 1, a process for preparing a photoresist polymer using the same, and said photoresist polymer:

<Chemical Formula>

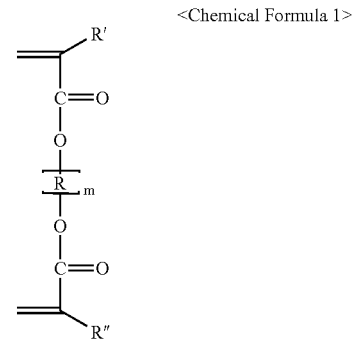

<Chemical Formula 1> wherein, R' and R" individually represent hydrogen or methyl; m represents a number of 1 to 10; and R is selected from the group consisting of straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group.

21 Claims, 2 Drawing Sheets

Fig.2

CROSS-LINKING MONOMERS FOR PHOTORESIST, AND PROCESS FOR PREPARING PHOTORESIST POLYMERS USING THE SAME

CROSS REFERENCE TO RELATED APPLICATIONS

This is a Continuation-In-Part application of U.S. patent application Ser. No. 09/465,111, filed Dec. 16, 1999 now abandoned, which is incorporated herein by reference in its entirety.

FIELD OF THE INVENTION

The present invention relates to cross-linking monomers for photoresist polymers, and processes for preparing photoresist polymers using the same. More specifically, it relates to cross-linking monomers for photoresist polymers which can noticeably improve the polymerization ratio of photoresist copolymers, and a process for preparing photoresist copolymers using the same.

BACKGROUND OF THE INVENTION

Recently, chemical amplification-type DUV (deep ultra violet) photoresists have proven to be useful to achieve high sensitivity in processes for preparing micro-circuits in the manufacture of semiconductors. These photoresists are prepared by blending a photoacid generator with polymer matrix macromolecules having acid labile structures.

According to the reaction mechanism of such a photoresist, the photoacid generator generates acid when it is irradiated by the light source, and the main chain or branched chain of the polymer matrix in the exposed portion is reacted with the generated acid to be decomposed or cross-linked, so that the polarity of the polymer is considerably altered. This alteration of polarity results in a solubility difference in the developing solution between the exposed area and the unexposed area, thereby forming a positive or negative image of a mask on the substrate.

In some photoresists, functional groups on the main chain or branched chain of one polymer are cross-linked with the main chain or branched chain of another polymer in the matrix. A cross-linker is therefore added to the photoresist to promote cross-linking between the polymers.

However, a cross-linking monomer can also be used to promote bonding between the monomers constituting a photoresist polymer, thereby enhancing the yield of the photoresist polymer. For example, when 20 g of monomer is used in the polymerization reaction without using a cross-linker, about 4.8 g of a polymer having molecular weight of about 6,000 is obtained (yield: 24%). When the amount of the monomer is increased to 40 g, the amount of the polymer obtained is only about 6 g (i.e., the yield is abruptly lowered to about 15%). Thus, in order to prepare photoresist polymer in a large scale, it is desirable to use a cross-linking monomer to increase the yield and make production of the photoresist polymer commercially reasonable.

SUMMARY OF THE INVENTION

The object of the present invention is to provide a cross-linking monomer for a photoresist polymer which can noticeably improve the polymerization yield of the photoresist polymer.

Another object of the present invention is to provide a process for preparing a photoresist polymer using said cross-linking monomer, and a photoresist polymer prepared therefrom.

Another object of the present invention is to provide photoresist compositions prepared by using polymers formed from the cross-linking monomer described above.

Still another object of the present invention is to provide a semiconductor element manufactured by using the photoresist composition described above.

BRIEF DESCRIPTION OF THE DRAWINGS

FIG. 2 shows a photoresist pattern obtained from Example 4.

DETAILED DESCRIPTION OF THE INVENTION

Figure 1:
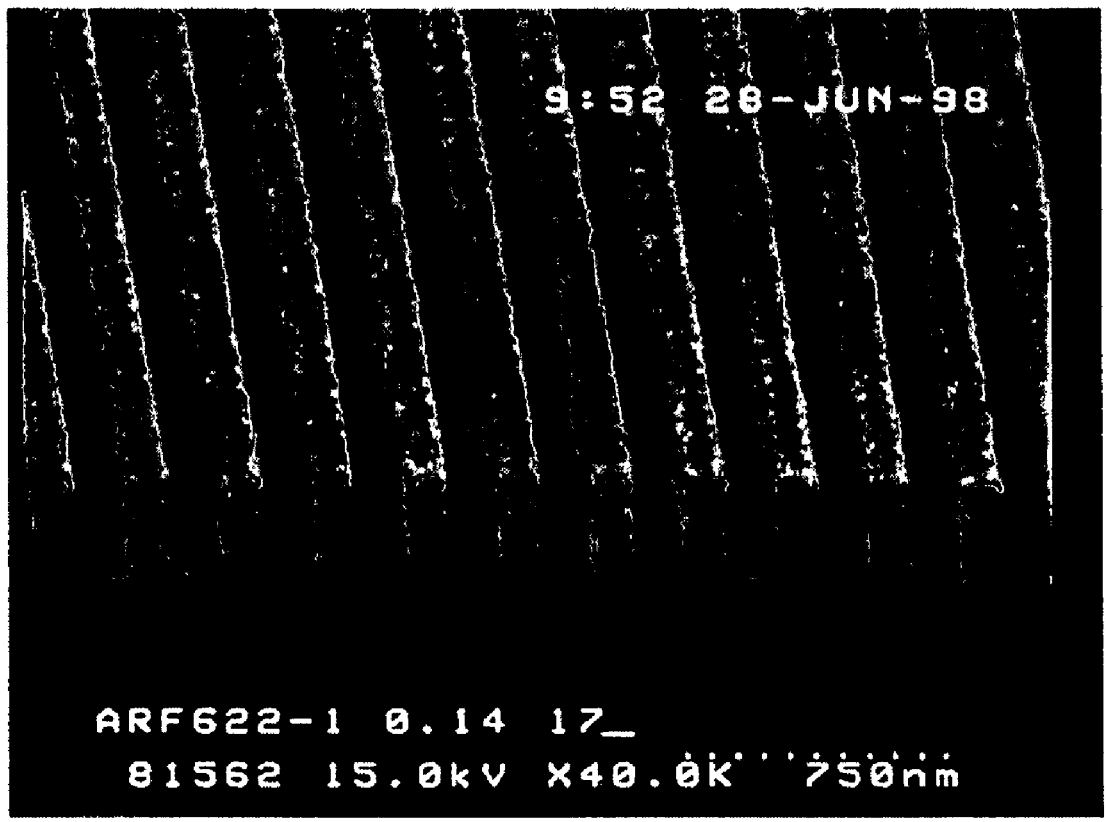
FIG. 1 shows a photoresist pattern obtained from Example 3.

To achieve the object described above, the present invention provides a cross-linking monomer represented by the following Chemical Formula 1:

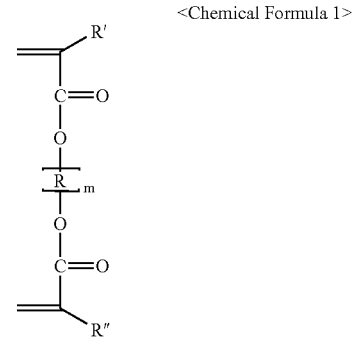

<Chemical Formula 1> wherein, R' and R" individually represent hydrogen or methyl; m represents a number from 1 to 10; and R is selected from the group consisting of straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group.

To achieve another object of the present invention, a process is provided for preparing a photoresist copolymer, which comprises the steps of (a) dissolving two or more photoresist comonomers and a cross-linking monomer of Chemical Formula 1 in an organic solvent, and (b) adding a polymerization initiator or a polymerization catalyst to the resultant solution to induce polymerization.

The inventors have performed intensive studies to achieve the objects of the invention described above, and have found that a compound represented by Chemical Formula 1 improves the polymerization yield of polymers by making the photoresist polymers cross-link to one another. The cross-linking monomer of the present invention is particularly effective to improve the polymerization yield of copolymers having an alicyclic olefin main chain.

The compound represented by Chemical Formula 1 has two double bonds, and each double bond combines with the other photoresist monomers to form cross-linking, thereby enhancing the polymerization yield of the photoresist polymer.

Preferably, the cross-linking monomer of Chemical Formula 1 is 1,3-butanediol diacrylate represented by Chemical Formula 2 or 1,4-butanediol diacrylate represented by Chemical Formula 3.

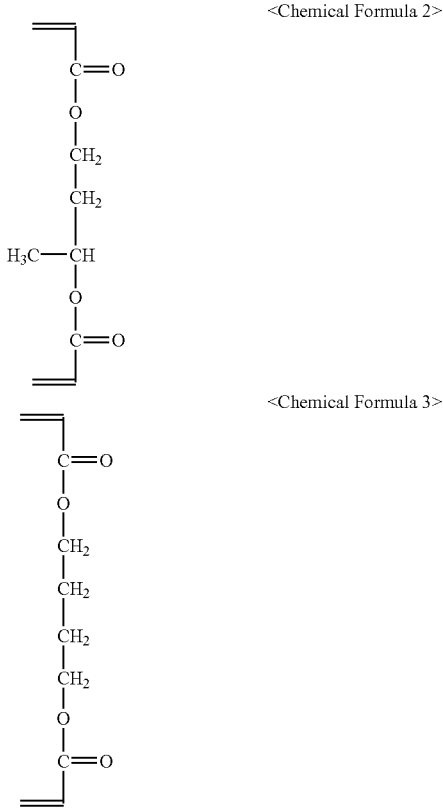

<Chemical Formula 2>

<Chemical Formula 3>

Preparation of Photoresist Polymers

The process for photoresist polymerization according to the present invention can be performed by adding a cross-linking monomer of Chemical Formula 1 to other photoresist monomers in the process for synthesizing a conventional photoresist copolymer.

For example, in the case of preparing a photoresist copolymer from alicyclic olefin derivatives, for example, as represented by the following Chemical Formula 4, polymerization is performed by dissolving two or more compounds represented by Chemical Formula 4 and a cross-linking monomer of Chemical Formula 1 in organic solvent, and adding a radical initiator or a metal catalyst to the resultant solution to induce polymerization:

Chemical Formula 4

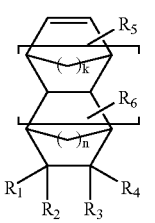

<Chemical Formula 4> wherein, k and n individually represent the number 1 or 2; p represents a number from 0 to 5, $R_5$ and $R_6$ individually represent hydrogen or methyl, $R_1$, $R_2$, $R_3$ and $R_4$ individually represent hydrogen, straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group.

It is desirable to carry out the polymerization reaction at a temperature between 60° C. and 130° C. and at a pressure between 0.0001 and 5 atm under nitrogen or argon atmosphere.

Bulk polymerization or solution polymerization may be employed as a polymerization process, and cyclohexanone, methyl ethyl ketone, benzene, toluene, dioxane, tetrahydrofuran, propylene glycol methyl ether acetate and/or dimethylformamide, or mixtures thereof, may be used as a polymerization solvent. As a polymerization initiator, benzoyl peroxide, 2,2'-azobisisobutyronitrile (AIBN), acetyl peroxide, lauryl peroxide, tert-butyl peracetate, tert-butyl hydroperoxide, di-tert-butyl peroxide, or the like may be used.

A desirable photoresist polymer prepared by using the polymerization process of the present invention is represented by following Chemical Formula 5:

Chemical Formula 5

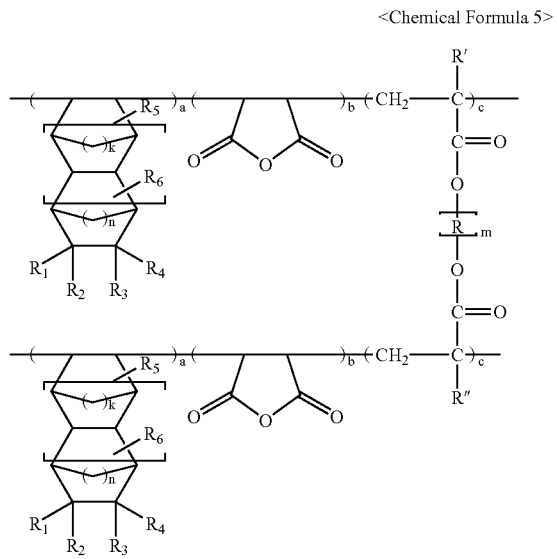

<Chemical Formula 5> wherein, k and n individually represent the number 1 or 2; m represents a number from 1 to 10; p represents a number from 0 to 5; R', R", $R_5$ and $R_6$ individually represent hydrogen or methyl; R is selected from the group consisting of straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; $R_1$, $R_2$, $R_3$ and $R_4$ are individually selected from the group consisting of hydrogen, straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group, and the ratio a:b:c is preferably 1–50 mol %:10–50 mol %:0.1–20 mol %.

The molecular weight of the photoresist polymer represented by Chemical Formula 5 is preferably 3,000 to 100,000.

The photoresist polymer according to the present invention shows no significant difference in photolithographic performance from a polymer formed without a cross-linking monomer. However, when the cross-linking monomer of the present invention is employed, the polymerization yield is noticeably increased.

For example, when 20 g of comonomer is employed in the polymerization without using a cross-linking monomer, about 4.8 g of a polymer having molecular weight of about 6,000 is obtained (yield: 24%). When the amount of the comonomer is increased to 40 g, the amount of the polymer obtained is only about 6 g (i.e., the yield is abruptly lowered to about 15% when larger quantities of reactants are used). Thus, merely increasing the quantity of reactants is not a suitable method for producing the copolymer on a large scale.

On the other hand, in the case of performing the same polymerization process using a cross-linking monomer according to the present invention, when 20 g of comonomer is used in the polymerization, about 7 g of the polymer having molecular weight of about 12,000 is obtained (yield: 35%); and, when the amount of the comonomer is increased to 40 g, the amount of the polymer obtained was about 14 g (yield: 35% i.e., no substantial change in the polymerization yield). The molecular weight of the obtained photoresist copolymer was 12,000, and the poly dispersity was about 2.0.

As shown above, higher yields can be obtained when the polymerization is performed using the cross-linking monomer of the present invention, thereby allowing the resultant photoresist polymer to be prepared on a large scale.

Preparation of Photoresist Compositions

A photoresist composition can be prepared according to the present invention by mixing a photoresist polymer of the present invention with an organic solvent. Cyclohexanone, methyl 3-methoxypropionate, ethyl 3-ethoxypropionate, propylene glycol methyl ether acetate, 2-methoxyethyl acetate, 2-heptanone, isobutyl methyl ketone, or the other conventional organic solvents may be used.

Optionally, a small amount of a photoacid generator may also be added to the photoresist composition. Examples of suitable photoacid generators, including sulfide or onium type photoacid generators, such as diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate, dibutylnaphthylsulfonium triflate, and the like.

Formation of a Photoresist Pattern

A photoresist composition prepared according to the present invention may be spin-coated on a silicon wafer to form a thin photoresist film thereon, which is then "soft-baked" in an oven or on a hot plate at 70° C. to 200° C., preferably at 80° C. to 150° C., for 1 to 5 minutes, and then exposed to patterned light by using a deep ultraviolet exposer or an excimer laser exposer. As the light source, ArF, KrF, E-beam, X-ray, EUV (extremely ultraviolet), DUV (deep ultraviolet) or the like may also be used, and the energy of light exposure is preferably from 1 to 100 mJ/cm$^2$.

Then, the thin photoresist film is "post-baked" at 10° to 200° C., preferably at 100° C. to 200° C., and the resultant material is impregnated with 2.38 wt % or 2.5 wt % aqueous TMAH developing solution for a predetermined time, preferably for 40 seconds, to obtain an ultramicro pattern.

A semiconductor element with high integrity can be manufactured by using the photoresist pattern according to the present invention.

The above description discloses only certain embodiments related to processes for preparing a photoresist copolymer or a photoresist composition by using a cross-linking monomer. It should be understood that the present invention is not restricted to these examples, but includes using the cross-linking monomer of the present invention in any process for producing a conventional photoresist copolymer or photoresist composition.

DETAILED DESCRIPTION OF PREFERRED EMBODIMENT

The invention is described in more detail by referring to the examples below, but it should be noted that the present invention is not restricted to these examples.

EXAMPLE 1

Synthesis of poly(maleic anhydride/2-hydroxyethyl 5-norbornene-2-carboxylate/tert-butyl 5-norbornene-2-carboxylate/5-norbornene-2-carboxylic acid/1,3-butanediol diacrylate)

First, (i) 2-hydroxyethyl 5-norbornene-2-carboxylate (0.1 mole), (ii) tert-butyl 5-norbornene-2-carboxylate (0.85 mole), (iii) 5-norbornene-2-carboxylic acid (0.05 mole), (iv) 1,3-butanediol diacrylate (0.1 mole), which is a cross-linking monomer within the scope of Chemical Formula 2, and (v) maleic anhydride (1.0 mole) are dissolved in tetrahydrofuran.

2,2'-Azobisisobutyronitrile (AIBN) (6.16 g) is added to the resultant solution as a polymerization initiator, and the mixture is reacted at 67° C. for 10 hours under an atmosphere of nitrogen or argon. The polymer thus obtained is precipitated from ethyl ether or hexane, and dried to obtain poly(maleic anhydride/2-hydroxyethyl 5-norbornene-2-carboxylate/tert-butyl 5-norbornene-2-carboxylate/5-norbornene-2-carboxylic acid/1,3-butanediol diacrylate) of following Chemical Formula 6 (yield: 35%):

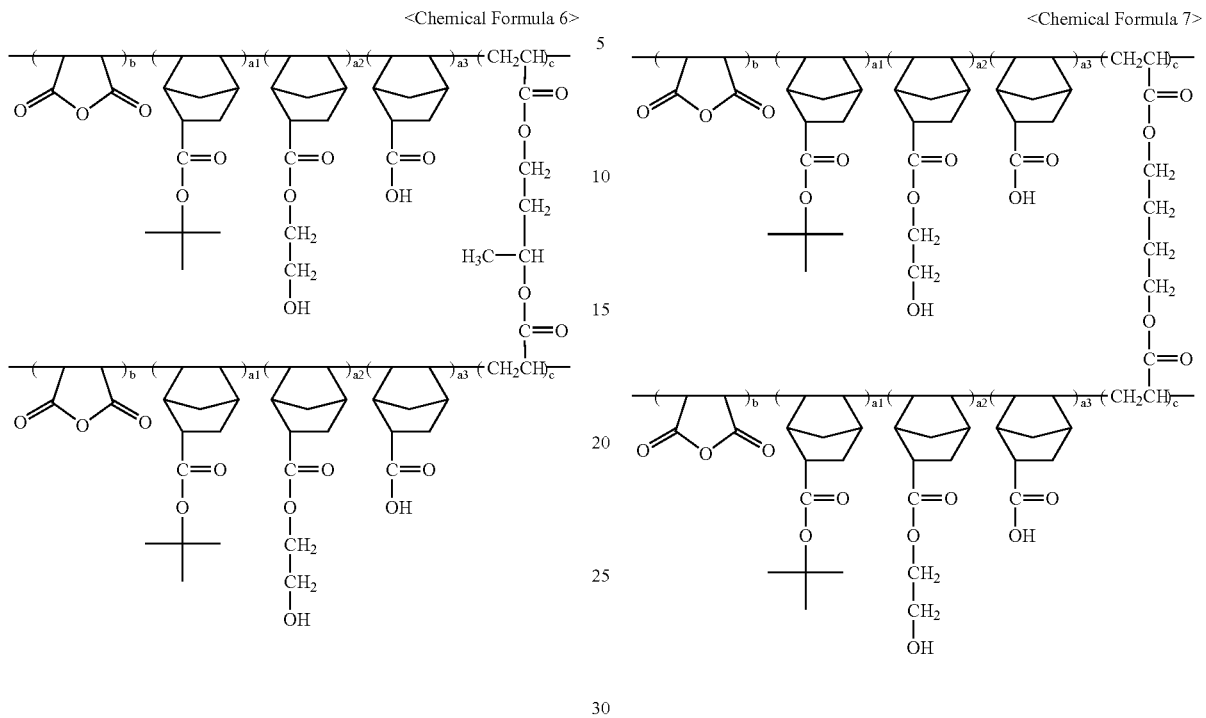

The molar ratio a1:a2:a3:b:c is 0.405:0.048:0.024:0.476:0.047.

EXAMPLE 2

Synthesis of poly(maleic an hydride/2-hydroxyethyl 5-norbornene-2-carboxylate/tert-butyl 5-norbornene-2-carboxylate/5-norbornene-2-carboxylic acid/1,4-butanediol diacrylate)

The procedure of Example 1 is repeated but using 1,4-butanediol diacrylate instead of 1,3-butanediol diacrylate, to obtain poly (maleic anhydride/2-hydroxyethyl 5-norbornene-2-carboxylate/tert-butyl 5-norbornene-2-carboxylate/5-norbornene-2-carboxylic acid/1,4-butanediol diacrylate) of following Chemical Formula 7:

The molar ratio a1:a2:a3:b:c is 0.405:0.048:0.024:0.476:0.047.

EXAMPLE 3

After dissolving the photoresist polymer of Chemical Formula 6, obtained from Example 1 (3.57 g), in ethyl 3-ethoxypropionate (25 g), triphenylsulfonium triflate (0.02 g) is added as a photoacid generator, and the resultant mixture is filtered through a 0.10 μm filter to prepare a photoresist composition.

The photoresist composition thus prepared is spin-coated on a silicon wafer, and soft-baked at 110° C. for 90 seconds. Then, after irradiating with light having exposure energy of 0.1 to 40 mJ/cm$^2$ using an ArF laser exposer, the wafer is post-baked again at 110° C. for 90 seconds. When the post-baking is completed, it was developed in 2.38 wt % aqueous TMAH solution for 40 seconds, to obtain 0.14 μm L/S pattern (FIG. 1).

EXAMPLE 4

Figure 2:
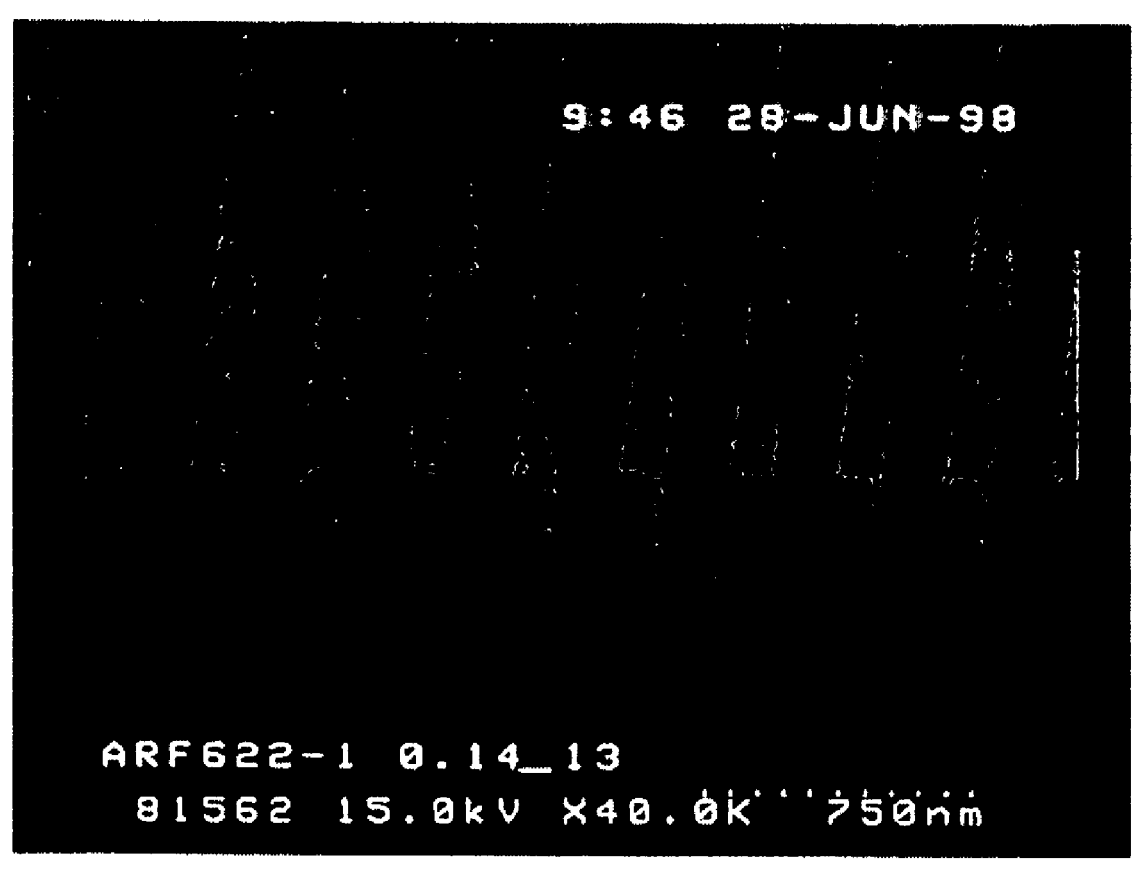

The procedure according to Example 3 is repeated but using the photoresist polymer of Chemical Formula 7 obtained from Example 2, instead of the polymer obtained from Example 1, to form a photoresist pattern. An ultramicro pattern of 0.14 μm L/S was obtained (FIG. 2).

What is claimed is:
1. A photoresist copolymer derived from a mixture of monomers comprising:
   (a) two or more alicyclic olefin derivatives, each having the formula:

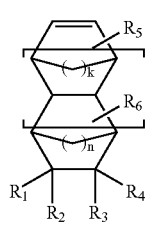

<Chemical Formula 4> wherein k and n is independently 1 or 2;

p is an integer from 0 to 5;

$R_5$ and $R_6$ are independently hydrogen or methyl; and $R_1$, $R_2$, $R_3$, and $R_4$ individually represent hydrogen, straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group, and (b) a cross-linking monomer of the formula:

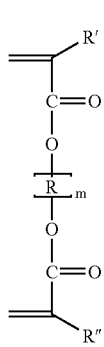

<Chemical Formula 1> wherein each of R' and R" is independently hydrogen or methyl;

m is an integer from 1 to 10; and

R is straight or branched $C_{1-10}$ alkyl, optionally comprising an ester, a ketone, a carboxylic acid, an acetal, a hydroxyl group or a combination thereof.

2. The photoresist copolymer according to claim 1 of the formula:

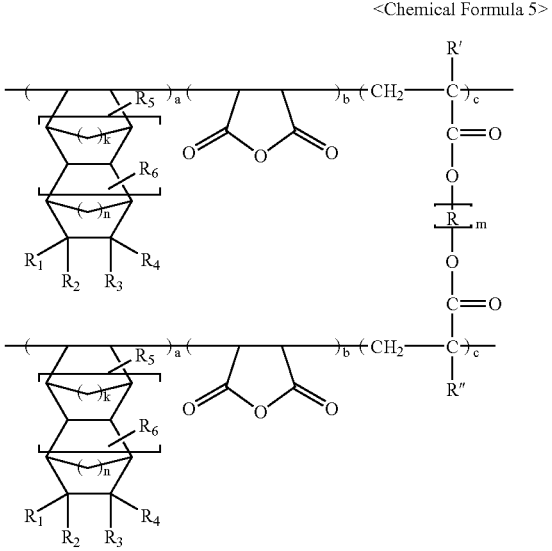

<Chemical Formula 5> wherein k, m, n, p, R, $R_1$, $R_2$, $R_3$, $R_4$, $R_5$, $R_6$, R', and R" are those defined in claim 1; and the ratio a:b:c is 1–50 mol %:10–50 mol %:0.1–20 mol %.

3. The photoresist composition comprising (i) a photoresist copolymer according to claim 1, and (ii) an organic solvent.

4. The photoresist composition according to claim 3, which further comprises a photoacid generator.

5. The photoresist composition according to claim 4, wherein the photoacid generator is one or more compound(s) selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate, and dibutylnaphtylsulfonium triflate.

6. A process for forming a photoresist pattern, which comprises the steps of (a) coating a photoresist composition according to claim 3 on a wafer, (b) exposing the wafer to patterned light by employing an exposer, and (c) developing the exposed wafer.

7. The process for forming a photoresist pattern according to claim 6, wherein the step (b) is carried out by using a light source selected from the group consisting of ArF, KrF, E-beam, X-ray, EUV (extremely ultraviolet) and DUV (deep ultraviolet).

8. The process according to claim 7, which further comprises baking step(s) before and/or after step (b).

9. The process according to claim 8, wherein the baking step(s) are performed at a temperature of 50° C. to 200° C.

10. The process according to claim 6, wherein the developing step (c) is carried out using an aqueous solution of TMAH (tetramethylamine hydroxide).

11. A semiconductor wafer comprising the photoresist pattern formed by using a process according to claim 6.

12. The photoresist copolymer according to claim 1 wherein said mixture of monomers further comprises maleic anhydride.

13. The photoresist copolymer according to claim 1 wherein the cross-linking monomer is 1,3-butanediol diacrylate or 1,4-butanediol diacrylate.

14. The photoresist polymer comprising poly(maleic anhydride/2-hydroxyethyl 5-norbornene-2-carboxylate/tert-butyl 5-norbornene-2-carboxylate/5-norbornene-2-carboxylic acid/1,3-butanediol diacrylate); or poly(maleic anhydride/2-hydroxyethyl 5-norbornene-2-carboxylate/tert-butyl 5-norbornene-2-carboxylate/5-norbornene-2-carboxylic acid/1,4-butanediol diacrylate).

15. A process for preparing a photoresist copolymer comprising admixing a mixture comprising at least two alicyclic monomers, a cross-linking monomer, and a polymerization initiator under polymerization reaction conditions sufficient to produce the photoresist copolymer, wherein each alicyclic monomer is of the formula:

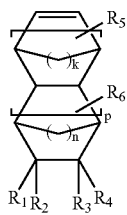

wherein
k and n is independently 1 or 2;
p is an integer from 0 to 5;
$R_5$ and $R_6$ are independently hydrogen or methyl; and
$R_1$, $R_2$, $R_3$, and $R_4$ individually represent hydrogen, straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group;

and the cross-linking monomer is of the formula:

wherein
each of R' and R'' is independently hydrogen or methyl;
m is an integer from 1 to 10; and
R is straight or branched $C_{1-10}$ alkyl, optionally comprising an ester, a ketone, a carboxylic acid, an acetal, a hydroxyl group or a combination thereof.

16. The process for preparing a photoresist copolymer according to claim 15, wherein the polymerization reaction is carried out under an atmosphere of nitrogen or argon.

17. The process for preparing a photoresist copolymer according to claim 15, wherein the polymerization reaction is carried out at a temperature between 60° C. and 130° C.

18. The process for preparing a photoresist copolymer according to claim 15, wherein the polymerization reaction is carried out under the pressure between 0.0001 and 5 atm.

19. The process for preparing a photoresist copolymer according to claim 15, wherein the mixture is dissolved in an organic solvent selected from the group consisting of cyclohexanone, methyl ethyl ketone, benzene, toluene, dioxane, tetrahydrofuran, propylene glycol methyl ether acetate, dimethylformamide, and a mixture thereof.

20. The process for preparing a photoresist copolymer according to claim 15, wherein the polymerization initiator is one or more compound(s) selected from the group consisting of 2,2-azobisisobutyronitrile (AIBN), acetyl peroxide, lauryl peroxide, tert-butyl peracetate, tert-butyl hydroperacetate and tert-butyl peroxide.

21. The process according to claim 15 wherein the mixture of monomers further comprises maleic anhydride.

* * * * *

UNITED STATES PATENT AND TRADEMARK OFFICE
CERTIFICATE OF CORRECTION

PATENT NO. : 7,208,260 B2  
APPLICATION NO. : 10/080507  
DATED : April 24, 2007  
INVENTOR(S) : Jung et al.

Page 1 of 2

It is certified that error appears in the above-identified patent and that said Letters Patent is hereby corrected as shown below:

Title Page, section (75) Inventors, 4th line, delete "Balk", and insert --Baik--;

Column 3, line 58, delete " 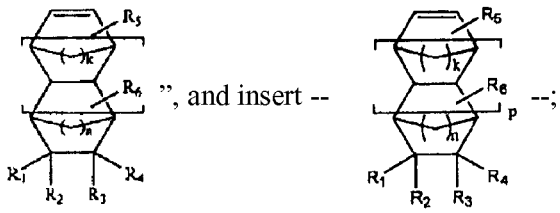 ", and insert -- --;

Column 4, line 35, delete " 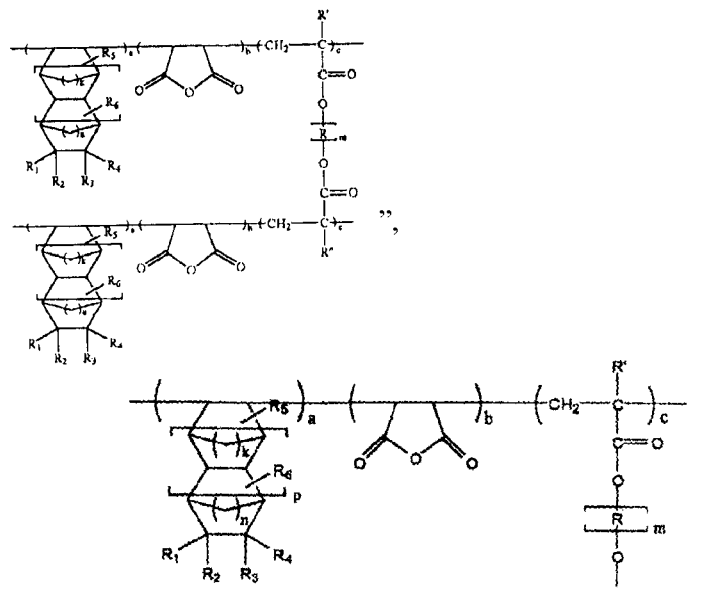 ", and insert -- --;

Column 7, line 51, delete "an hydride", and insert --anhydride--;

Claim 1, column 9, line 5, delete " 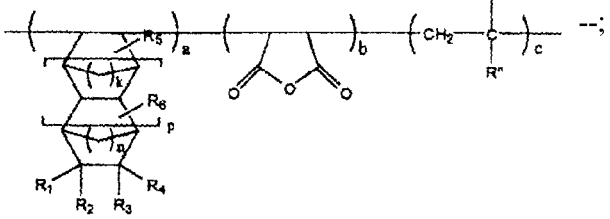 ", and insert -- 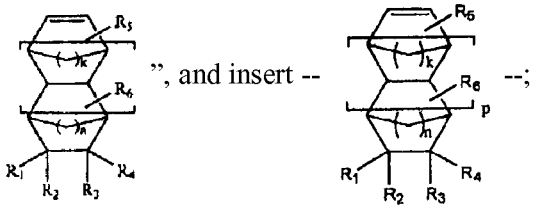 --;

UNITED STATES PATENT AND TRADEMARK OFFICE
CERTIFICATE OF CORRECTION

PATENT NO. : 7,208,260 B2
APPLICATION NO. : 10/080507
DATED : April 24, 2007
INVENTOR(S) : Jung et al.

It is certified that error appears in the above-identified patent and that said Letters Patent is hereby corrected as shown below:

Claim 2, column 10, line 5, delete " 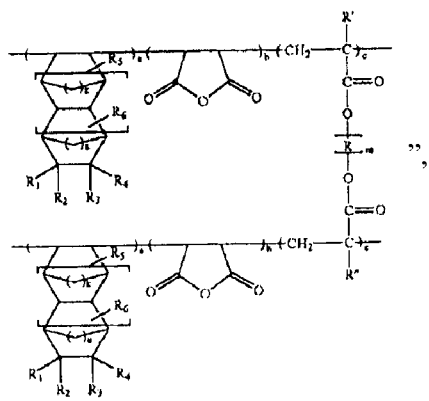 ", and insert -- 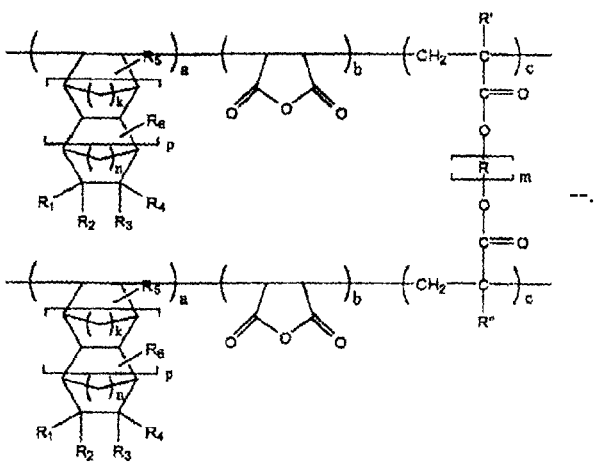 --.

Signed and Sealed this

Eighth Day of July, 2008

JON W. DUDAS
*Director of the United States Patent and Trademark Office*